United States Patent
Tokuda et al.

(10) Patent No.: US 8,230,721 B2
(45) Date of Patent: Jul. 31, 2012

(54) PARTICULATE MATTER DETECTION DEVICE

(75) Inventors: Masahiro Tokuda, Nagoya (JP); Takashi Egami, Nagoya (JP); Takeshi Sakuma, Nagoya (JP); Atsuo Kondo, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 340 days.

(21) Appl. No.: 12/715,617

(22) Filed: Mar. 2, 2010

(65) Prior Publication Data

US 2010/0229630 A1 Sep. 16, 2010

(30) Foreign Application Priority Data

Mar. 12, 2009 (JP) ................................. 2009-058849

(51) Int. Cl.
*G01N 37/00* (2006.01)
(52) U.S. Cl. .................................................... 73/28.01
(58) Field of Classification Search .................. 73/28.01
See application file for complete search history.

(56) References Cited

U.S. PATENT DOCUMENTS 4,656,832 A * 4/1987 Yukihisa et al. ................ 60/303

FOREIGN PATENT DOCUMENTS

JP 60-123761 A1 7/1985

OTHER PUBLICATIONS

U.S. Appl. No. 12/701,774, filed Feb. 8, 2010, Egami, et al.
U.S. Appl. No. 12/715,598, filed Mar. 2, 2010, Tokuda, et al.
U.S. Appl. No. 12/715,644, filed Mar. 2, 2010, Tokuda, et al.
U.S. Appl. No. 12/715,661, filed Mar. 2, 2010, Tokuda, et al.

* cited by examiner

*Primary Examiner* — Hezron E Williams
*Assistant Examiner* — Rodney T Frank
(74) *Attorney, Agent, or Firm* — Burr & Brown

(57) ABSTRACT

A particulate matter detection device (100) includes a detection device body (1) extending in one direction and having at least one through-hole (2) that is formed at one end (1*a*), at least one pair of electrodes buried in the wall of the body (1) that defines the through-hole (2), and covered with a dielectric, lines respectively extending from the pair of electrodes toward the other end (1*b*), a takeout lead terminal (12*a*) of one electrode of the pair of electrodes disposed on the surface of the other end (1*b*), a takeout lead terminal (11*a*) of the other electrode of the pair of electrodes between one end (1*a*) and the other end (1*b*), and an electric wire (21) provided with an electric wire securing member (31) at its tip portion, and bonded to the takeout lead terminal (11*a*) through the electric wire securing member (31).

8 Claims, 5 Drawing Sheets

PARTICULATE MATTER DETECTION DEVICE

BACKGROUND OF THE INVENTION

The present invention relates to a particulate matter detection device. More particularly, the present invention relates to a particulate matter detection device that prevents separation of a high-voltage electric wire due to vibrations during use, has a reduced size, shows only a small measurement error, and can be produced inexpensively.

A flue exhaust gas or a diesel engine exhaust gas contains a particulate matter (PM) such as soot or the like and has been a cause for air pollution. A filter (diesel particulate filter: DPF) made of a ceramic or the like has been widely used to remove the particulate matter. The ceramic DPF can be used for a long period of time, but may suffer defects such as cracks or erosion due to thermal deterioration or the like, so that a small amount of particulate matter may leak from the DPF. It is very important to immediately detect such occurrence of the defects and to recognize the abnormality of a device from the viewpoint of preventing air pollution.

Such defects may be detected by providing a particulate matter detection device on the downstream side of the DPF (e.g., JP-A-60-123761).

SUMMARY OF THE INVENTION

According to JP-A-60-123761, the particulate matter is charged by causing a corona discharge, and an ion current due to the charged particulate matter is measured to determine the amount of the particulate matter. According to this method, since the ion current due to the charged particulate matter is weak, there has been a problem that a large-scale detection circuit is required for detecting such a weak ion current so that cost increases. Moreover, since the particulate matter cannot be effectively charged when the exhaust gas flow rate is large, the amount of particulate matter measured may be smaller than the amount of particulate matter actually contained in the exhaust gas. Therefore, there has also been a problem that a large error occurs.

In order to solve the above problems, a particulate matter detection device that is formed of a ceramic and extends in one direction has been proposed, including a through-hole and a pair of electrodes that are used to detect a particulate matter and formed at one end, and a takeout lead terminal that is formed at the other end (Japanese Patent Application No. 2008-246461). A ceramic plate-shaped particulate matter detection device 200 shown in FIGS. 10A and 10B is an example of such a particulate matter detection device. A through-hole 62 is formed at one end 65 of a detection device body 61, and a pair of electrodes are buried in the detection device body 61 so that the pair of electrodes are positioned on either side of the through-hole 62 sandwiched. The particulate matter detection device 200 is configured so that the particulate matter contained in an exhaust gas that flows into the through-hole 62 is caused to adhere to the wall surface of the through-hole 62 or the like by applying a voltage between the pair of electrodes, and the impedance of the wall surface of the through-hole is measured to detect the amount of particulate matter adhering to the wall surface of the through-hole 62, for example. A takeout lead terminal 63 connected to one of the pair of electrodes is disposed at an end (the other end) 66 opposite to the end in which the through-hole 62 is formed, and a takeout lead terminal 64 connected to the other of the pair of electrodes is disposed on the surface of the detection device body 61 between one end and the other end.

The takeout lead terminals 63 and 64 are connected to electric wires provided from the outside of the particulate matter detection device 200. FIG. 10A is a front view schematically showing a particulate matter detection device. FIG. 10B is a side view schematically showing a particulate matter detection device.

When detecting a particulate matter using the above particulate matter detection device, it is preferable to generate plasma in the through-hole by applying a high voltage between the pair of electrodes to charge the particulate matter, and cause the charged particulate matter to adhere to the inner wall surface of the through-hole to detect the amount of particulate matter adhering to the inner wall surface of the through-hole, for example. At this time, when applying a high voltage between the pair of electrodes, the takeout lead terminal 64 disposed on the surface of the detection device body 61 between one end and the other end is preferably used as a high-voltage electrode. Therefore, it is necessary to connect a high-voltage electric wire to the takeout lead terminal 64 that is disposed on the surface of the detection device body 61 between one end and the other end. However, when installing the particulate matter detection device in an automobile, the particulate matter detection device is subjected to large vibrations caused by the engine, and also the connection section may be exposed to a high temperature. Therefore, there has been a problem that the electric wire may be separated due to vibrations during use when using a known simple connection method.

The present invention was conceived in view of the above problems. An object of the present invention is to provide a particulate matter detection device that has a reduced size, shows only a small measurement error, and can be produced inexpensively.

To achieve the above object, according to the present invention, there is provided a particulate matter detection device as follows.

[1] A particulate matter detection device comprising a detection device body that extends in one direction and has at least one through-hole that is formed at one end, at least one pair of electrodes that are buried in the wall of the detection device body that defines the through-hole, and are covered with a dielectric, lines that respectively extend from the pair of electrodes toward the other end of the detection device body, a takeout lead terminal of one electrode of the pair of electrodes, the takeout lead terminal of the one electrode being disposed on the surface of the other end of the detection device body, and connected to the line that extends from the one electrode, a takeout lead terminal of the other electrode of the pair of electrodes, the takeout lead terminal of the other electrode being disposed on the surface of the detection device body between the one end and the other end, and connected to the line that extends from the other electrode, and an electric wire that is provided with an electric wire securing member at its end, and bonded to the takeout lead terminal of the other electrode through the electric wire securing member, the particulate matter detection device being configured so that the particulate matter contained in a fluid that flows into the through-hole can be electrically adsorbed on the wall surface of the through-hole by applying a voltage of 50 to 200 kV/cm between the pair of electrodes through the takeout lead terminals using the other electrode as a high-voltage electrode, and the particulate matter adsorbed on the wall surface of the through-hole can be detected by measuring a change in electrical properties of the wall of the detection device body that defines the through-hole.

[2] The particulate matter detection device according to [1], wherein the electric wire securing member is a metal plate that is bent to sandwich and secure an end of the electric wire.

[3] The particulate matter detection device according to [2], wherein the electric wire securing member is formed by bending a T-shaped metal plate that includes a rectangular wing area and a rectangular body area that extends from the center of the wing area in the direction perpendicular to the longitudinal direction of the wing area so that each end of the wing area is folded toward the center of the wing area, and the end of the electric wire is sandwiched and secured between each end of the wing area and the center of the wing area.

[4] The particulate matter detection device according to [2] or [3], wherein the electric wire securing member is bonded to the takeout lead terminal of the other electrode through a bonding metal plate.

[5] The particulate matter detection device according to [2] or [3], wherein the electric wire securing member is bonded to the takeout lead terminal of the other electrode through a conductive adhesive.

[6] The particulate matter detection device according to [1], wherein the electric wire securing member is a metal paste that covers the end of the electric wire, and the end of the electric wire is bonded to the takeout lead terminal of the other electrode through the metal paste.

The particulate matter detection device according to the present invention is configured so that at least one pair of electrodes are buried in the wall of the detection device body that defines the through-hole, and a particulate matter present in the through-hole can be charged by causing a discharge to occur in the through-hole by applying a voltage between the pair of electrodes, and electrically adsorbed on the electrode. The particulate matter detection device according to the present invention can thus measure only the mass of particulate matter contained in exhaust gas that flows on the downstream side of a DPF and has flowed into the through-hole. Specifically, the particulate matter detection device according to the present invention does not directly measure the entire particulate matter contained in exhaust gas that flows on the downstream side of the DPF, but measures only particulate matter that has flowed into the through-hole. The amount of particulate matter contained in the entire exhaust gas can be roughly estimated from the measured value. Therefore, the particulate matter detection device can be reduced in size, and installed in a narrow space. Moreover, the particulate matter detection device can be produced inexpensively.

Since the particulate matter detection device according to the present invention allows only part of exhaust gas (a particulate matter) to be introduced into the through-hole, the particulate matter introduced into the through-hole can be effectively charged even if the total flow rate of exhaust gas that flows on the downstream side of the DPF is large, so that a measured value with only a small error can be obtained.

Since the detection device body is formed to extend in one direction and has the through-hole that is formed at one end of the detection device body, and at least one pair of electrodes are disposed (buried) at one end of the detection device body, only the through-hole and part of the pair of electrodes can be inserted into a pipe through which high-temperature exhaust gas flows while allowing the other end of the detection device body to be positioned outside the pipe. Therefore, an area such as takeout lead terminals of the pair of electrodes for which exposure to high temperature is not desirable can be positioned outside the pipe, so that the particulate matter can be detected accurately and stably.

Moreover, since the high-voltage electric wire is bonded to the takeout lead terminal, used for applying high-voltage electrode, disposed on the surface of the detection device body between one end and the other end of the detection device body through the electric wire securing member, the electric wire can be tightly bonded to a given takeout lead terminal using the electric wire securing member. Therefore, separation of the electric wire due to vibrations during use can be prevented.

DESCRIPTION OF EXEMPLARY EMBODIMENTS

Embodiments of the present invention are described in detail below with reference to the drawings. Note that the present invention is not limited to the following embodiments. Various modifications and improvements of the design may be appropriately made without departing from the scope of the present invention based on the knowledge of a person having ordinary skill in the art.

Figure 1A:
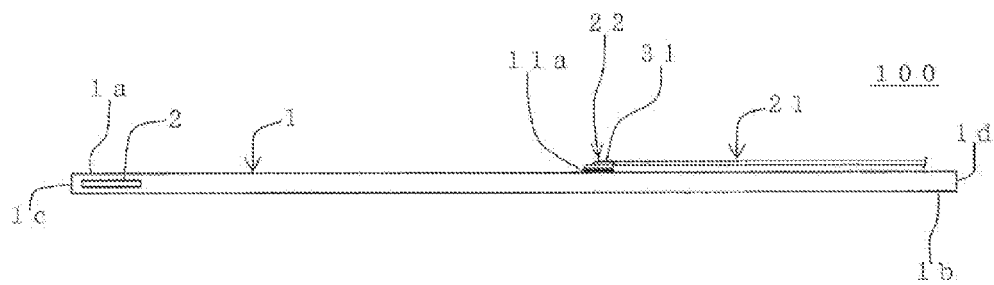
FIG. 1A is a front view schematically showing a particulate matter detection device according to one embodiment of the present invention.
Figure 1B:
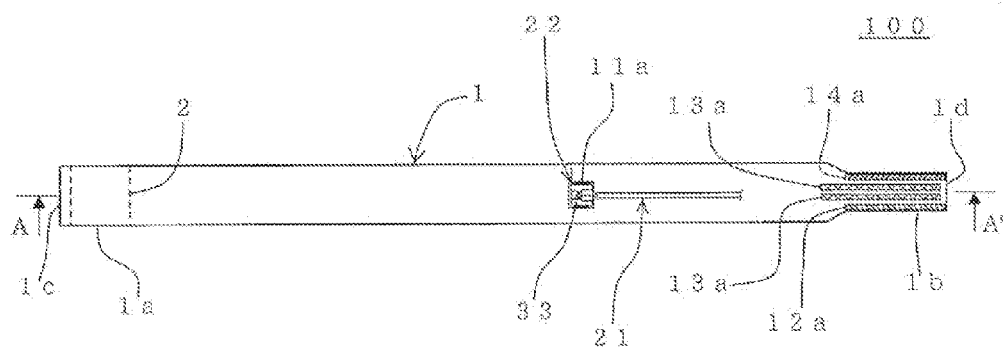
FIG. 1B is side view schematically showing a particulate matter detection device according to one embodiment of the present invention.
Figure 2A:
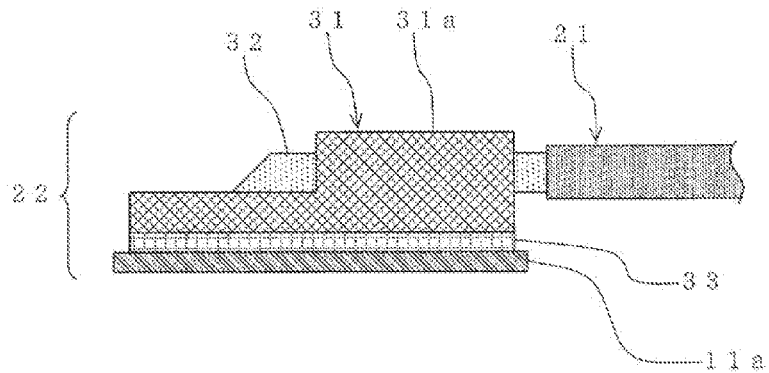
FIG. 2A is an enlarged schematic view showing the joint shown in FIG. 1A between the electric wire and the takeout lead terminal disposed on the surface of the detection device body between one end and the other end.
Figure 2B:
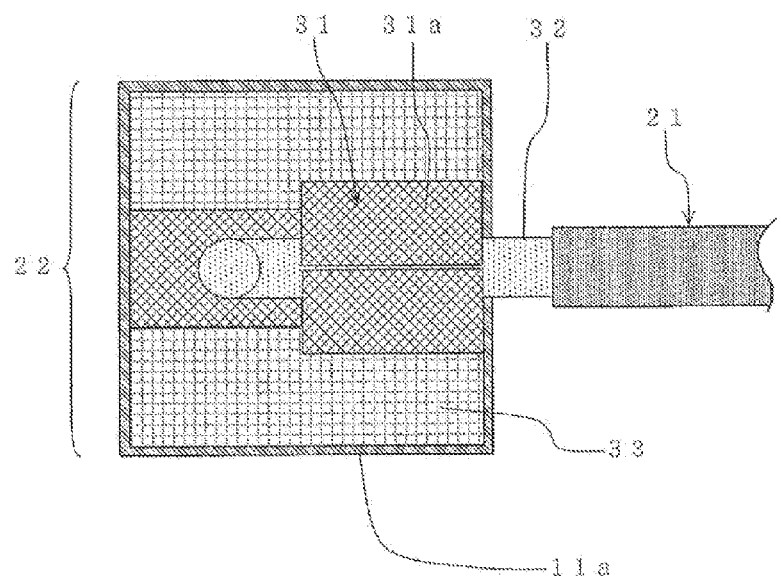
FIG. 2B is an enlarged schematic view showing the joint shown in FIG. 1B between the electric wire and the takeout lead terminal disposed on the surface of the detection device body between one end and the other end.
Figure 3:
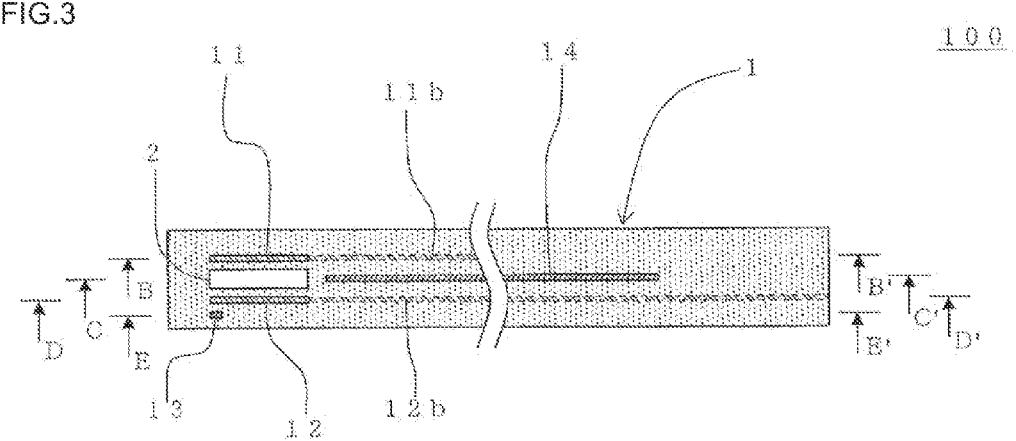
FIG. 3 is a schematic view showing a cross section cut along A-A' line of the particulate matter detection device according to one embodiment of the present invention shown in FIG. 1B.

FIG. 1A is a front view schematically showing a particulate matter detection device according to one embodiment of the present invention, and FIG. 1B is a side view schematically showing a particulate matter detection device according to one embodiment of the present invention. FIG. 2A is an enlarged schematic view showing a joint 22 shown in FIG. 1A between an electric wire 21 and a takeout lead terminal 11a disposed on the surface of a detection device body between one end 1a and the other end 1b. FIG. 2B is an enlarged schematic view showing the joint 22 shown in FIG. 1B between the electric wire 21 and the takeout lead terminal 11a disposed on the surface of the detection device body between one end 1a and the other end 1b. FIG. 3 is a schematic view showing a cross section cut along A-A' line of the particulate matter detection device according to one embodiment of the present invention shown in FIG. 1B.

As shown in FIGS. 1A, 1B, 2A, 2B, and 3, a particulate matter detection device 100 according to this embodiment includes a detection device body 1 that extends in one direction and has at least one through-hole 2 that is formed at one end 1a, a pair of electrodes 11 and 12 that are buried in the wall of the detection device body 1 that defines the through-hole 2, and are covered with a dielectric, lines 11b and 12b that respectively extend from the pair of electrodes 11 and 12 toward the other end 1b of the detection device body 1, a takeout lead terminal 12a of one electrode 12 of the pair of electrodes 11 and 12, the takeout lead terminal 12a being disposed on the surface of the other end 1b of the detection device body 1, and connected to the line 12b that extends from the one electrode 12, a takeout lead terminal 11a (hereinafter may be referred to as "high-voltage terminal") of the other electrode 11 of the pair of electrodes 11 and 12, the takeout lead terminal 11a being disposed on the surface of the detection device body 1 between one end 1a and the other end 1b, and connected to the line 11b that extends from the other electrode 11, and an electric wire 21 that is provided with an electric wire securing member 31 at its end 32, and bonded to the takeout lead terminal 11a of the other electrode 11 through the electric wire securing member 31. The particulate matter detection device 100 according to this embodiment allows the particulate matter contained in a fluid that flows into the through-hole 2 to be electrically adsorbed on the wall surface of the through-hole 2 by applying a voltage of 50 to 200 kV/cm between the pair of electrodes 11 and 12 through the takeout lead terminals 11a and 12a using the other electrode 11 as a high-voltage electrode, and detects the particulate matter adsorbed on the wall surface of the through-hole 2 by measuring a change in electrical properties of the wall of the detection device body 1 that defines the through-hole 2.

It is necessary that detection device body 1 has at least one through-hole 2, and may have two or more through-holes 2. It is also necessary that the particulate matter detection device 100 has at least one pair of electrodes, and may have two or more pairs of electrodes. In the particulate matter detection device 100 according to this embodiment, the pair of electrodes 11 and 12 are buried in the detection device body 1. The detection device body 1 is formed of a dielectric so that the pair of electrodes 11 and 12 are covered with the dielectric. Therefore, the particulate matter detection device 100 according to this embodiment can detect the particulate matter contained in exhaust gas or the like that passes through the through-hole 2.

The particulate matter detection device 100 according to this embodiment can thus measure the only mass of particulate matter contained in exhaust gas that flows on the downstream side of a DPF and has flowed into the through-hole 2. Specifically, the particulate matter detection device 100 according to this embodiment does not directly measure the entire particulate matter contained in exhaust gas that flows on the downstream side of the DPF, but measures only the particulate matter that has flowed into the through-hole 2. The amount of particulate matter contained in the entire exhaust gas can be roughly estimated from the measured value. Therefore, the particulate matter detection device can be reduced in size, and installed in a narrow space. Moreover, the particulate matter detection device can be produced inexpensively. Furthermore, since the particulate matter detection device according to the present invention allows only part of exhaust gas (a particulate matter) to be introduced into the through-hole, particulate matter introduced into the through-hole can be effectively charged even if the total flow rate of exhaust gas that flows on the downstream side of the DPF is large, so that a measured value with only a small error can be obtained. Further, since the detection device body is formed to extend in one direction and has the through-hole that is formed at one end of the detection device body, and at least one pair of electrodes are disposed (buried) at one end of the detection device body, only the area in which the through-hole and the pair of electrodes are formed can be inserted into a pipe through which high-temperature exhaust gas flows while allowing the other end of the detection device body to be positioned outside the pipe. Therefore, an area such as takeout lead terminals of the pair of electrodes for which exposure to high temperature is not desirable can be positioned outside the pipe, so that particulate matter can be detected accurately and stably. Since the high-voltage electric wire 21 is bonded to the takeout lead terminal (high-voltage terminal) 11a (i.e., the takeout lead terminal of the electrode 11 to which a high voltage is applied) disposed on the surface of the detection device body 1 between one end 1a and the other end 1b through the electric wire securing member 31, the electric wire 21 can be tightly bonded to a given takeout lead terminal (high-voltage terminal 11a) using the electric wire securing member 31 so that separation of the electric wire 21 does not occur even if vibrations occur during use.

The particulate matter detection device 100 according to this embodiment includes the high-voltage terminal 11a that is disposed on the surface of the detection device body 1 between one end 1a and the other end 1b, and connected to the line 11b that extends from the other electrode 11, and the electric wire 21 that is provided with the electric wire securing member 31 at its end portion 32, and bonded to the high-voltage terminal 11a through the electric wire securing member 31. When directly brazing or welding the electric wire 21 to which a high voltage is applied to the high-voltage terminal 11a, the electric wire 21 may be removed from the high-voltage terminal 11a due to the difference in coefficient of thermal expansion (brazing), or the surface of the detection device body is damaged around the high-voltage terminal 11a when welding. The term "brazing" refers to a method that melts an alloy (filler metal) having a melting point lower than that of a bonding target member (matrix), and bonds the member without melting the matrix by utilizing the melted alloy as an adhesive. The term "welding" refers to a method that melts/unites two or more members by heating or pressurizing the members so that the joint area has continuity. On the other hand, since the particulate matter detection device 100 according to this embodiment is configured so that the electric wire securing member 31 is disposed at the end 32 of the electric wire 21, and bonded to the high-voltage terminal 11a, removal due to the difference in coefficient of thermal expansion or damage to the surface of the detection device body does not occur, so that the electric wire 21 can be tightly bonded to the high-voltage terminal 11a. This makes it possible to prevent separation of the high voltage electric wire (electric wire 21) due to vibrations during use.

The electric wire securing member 31 and the high-voltage terminal 11a are preferably bonded by bonding the electric wire securing member 31 to the high-voltage terminal 11a through a bonding metal plate 33. At this time, it is preferable to bond the bonding metal plate 33 to the high-voltage terminal 11a by brazing, and bond the electric wire securing member 31 to the bonding metal plate 33 by welding. This makes it possible to tightly bond the electric wire to the high-voltage terminal. The electric wire securing member 31 is preferably spot-welded to the bonding metal plate 33. The bonding metal plate 33 is preferably bonded to the high-voltage terminal 11a by brazing since it is possible to select a material that has a coefficient of thermal expansion similar to that of the high-voltage terminal 11a. If the bonding metal plate 33 is welded to the high-voltage terminal 11a, the high-voltage terminal 11a may be damaged. The electric wire securing member 31 is preferably welded to the bonding metal plate 33 since the bonding strength can be increased. If the electric wire securing member 31 on which the electric wire is secured is brazed and bond to the bonding metal plate 33, the electric wire needs to be exposed to a high temperature during brazing so that the insulating coating of the electric wire may deteriorate.

Examples of the material for the bonding metal plate 33 include kovar, stainless steel, iron, nickel, platinum, copper, gold, molybdenum, tungsten, and the like. Among these, it is preferable to use kovar that has a coefficient of thermal expansion close to that of alumina. The thickness of the bonding metal plate 33 is preferably 50 to 300 μm. The size of the bonding metal plate 33 is preferably 50 to 150% of the area of the high-voltage terminal 11a. The shape of the bonding metal plate 33 is not particularly limited, but is preferably a polygon such as quadrangle, a circle, an ellipse, or the like. It is more preferable that the bonding metal plate 33 have the same shape as that of the high-voltage terminal 11a.

The electric wire securing member and the high-voltage terminal may be bonded to each other by bonding the electric wire securing member to the high-voltage terminal through a conductive adhesive. Examples of the conductive adhesive include an adhesive that contains a metal powder such as nickel or aluminum, and the like. Note that the electric wire securing member and the high-voltage terminal are preferably bonded using the bonding metal plate instead of using the conductive adhesive.

The electric wire securing member 31 is preferably a metal plate 31a that is bent to sandwich and secure the tip portion 32 of the electric wire 21. The electric wire 21 can be reliably secured using the electric wire securing member 31 by wrapping around and securing the tip portion 32 of the electric wire 21 using the metal plate 31a. The electric wire securing member 31 is preferably formed by bending the metal plate 31a to sandwich and secure the end 32 of the electric wire 21. This means bending the metal plate 31a to sandwich the electric wire 21, and securing the electric wire 21 using the metal plate 31a. In other words, the electric wire 21 is swaged using the metal plate 31a. The thickness of the metal plate 31a is preferably 50 to 500 μm.

Examples of the material for the electric wire securing member 31 include stainless steel, kovar, iron, nickel, platinum, copper, gold, molybdenum, tungsten, and the like. Among these, it is preferable to use stainless steel from the viewpoint of strength and corrosion resistance. The size of the electric wire securing member 31 that has been bent and bonded to the high-voltage terminal is preferably 80 to 130% of the size of the high-voltage terminal 11a. This makes it possible to tightly bond the electric wire securing member 31 to the high-voltage terminal 11a. The size of the electric wire securing member 31 that is not bent is preferably 100 to 200% of the size of the high-voltage terminal 11a. This ensures that the electric wire securing member 31 that has been bent and bonded to the high-voltage terminal has a size within the above preferable range.

Figure 4:
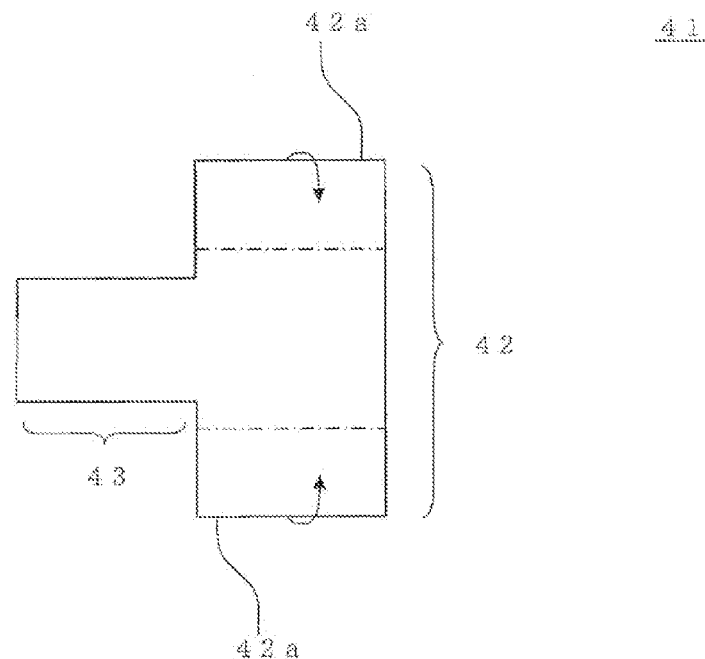
FIG. 4 is a plan view schematically showing a T-shaped metal plate that forms an electric wire securing member used in a particulate matter detection device according to one embodiment of the present invention.

As shown in FIG. 4, the electric wire securing member 31 is preferably formed by bending a T-shaped metal plate 41 that includes a rectangular wing area 42 and a rectangular body area 43 that extends from the center of the wing area 42 in the direction perpendicular to the longitudinal direction of the wing area 42 so that each end 42a of the wing area 42 is folded toward the center of the wing area 42 (see FIGS. 2A and 2B). The end 32 of the electric wire 21 is preferably sandwiched and secured between each end 42a of the wing area 42 and the center of the wing area 42. As shown in FIG. 4, the T-shaped metal plate 41 is formed so that the rectangular body area 43 extends from the rectangular wing area 42 in the same plane as the wing area 42. FIG. 4 is a plan view schematically showing the T-shaped metal plate 41 that forms the electric wire securing member 31 used in the particulate matter detection device according to one embodiment of the present invention.

According to this configuration, since the electric wire securing member 31 is formed by bending the wing area 42 of the T-shaped metal plate 41, the electric wire securing member 31 can advantageously be easily and quickly formed. The electric wire securing member 31 that is not bent preferably has a planar shape in the shape of the letter "T". Note that the planar shape of the electric wire securing member 31 is not limited thereto. The electric wire securing member 31 may have a polygonal such as quadrangular shape, or may be in the shape of the letter "H" (i.e., a shape having two bonding areas), for example.

Figure 5:
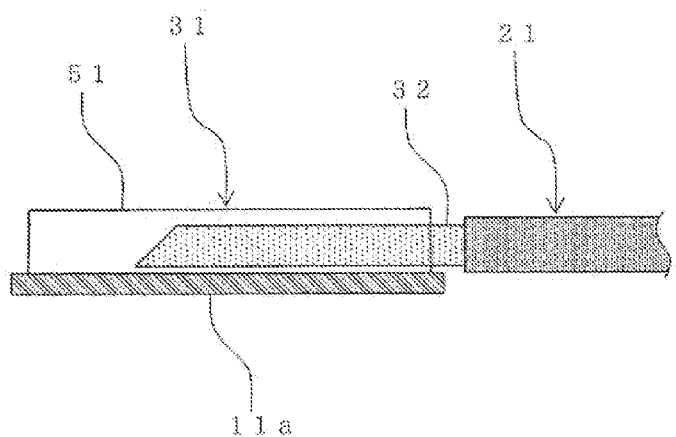
FIG. 5 is an enlarged schematic front view showing a joint between an electric wire and a takeout lead terminal disposed on the surface of a detection device body between one end and the other end in a particulate matter detection device according to another embodiment of the present invention.

In the particulate matter detection device 100 according to this embodiment, the electric wire securing member 31 is formed using the T-shaped metal plate 41. Note that, as shown in FIG. 5, the electric wire securing member 31 may be a metal paste 51 that covers the tip portion 32 of the electric wire 21, and the tip portion 32 of the electric wire 21 may be bonded to the high-voltage terminal (i.e., the takeout lead terminal of the other electrode) 11a through the metal paste 51. Examples of the metal paste 51 can include a silver paste, a platinum paste, and the like. When using the metal paste as the electric wire securing member, after applying the metal paste to the high-voltage terminal, the product is placed in a heating furnace. The metal paste is then dried at 100° C. for one hour to achieve the desired bonding strength. FIG. 5 is an enlarged schematic front view showing the joint 22 between the electric wire 21 and the takeout lead terminal 11a disposed on the surface of the detection device body between one end 1a and the other end 1b in the particulate matter detection device according to another embodiment of the present invention. The particulate matter detection device according to this embodiment is the same as the particulate matter detection device according to one embodiment of the present invention, except that the metal paste 51 is used as the electric wire securing member 31.

In the particulate matter detection device 100 according to this embodiment, the electric wire 21 includes a conductive section 23 that is formed of a conductor, and an insulating coating 24 that is formed of an insulator and surrounds the outer circumferential surface of the conductive section 23. The insulating coating 24 is not provided at one end of the conductive section 23 in order to electrically connect the conductive section 23 to the high-voltage terminal 11a. The area in which the insulating coating 24 is not provided is the tip portion 32. The end of the electric wire 21 opposite to the end bonded to the high-voltage terminal 11a is preferably connected to a high-voltage power supply, a measurement section that measures the impedance, or the like during use. The length of the end 32 is preferably 30 to 200% of the width of the high-voltage terminal 11a. The width of the high-voltage terminal 11a used herein refers to the dimension of the high-voltage terminal 11a in the longitudinal direction of the electric wire 21 in a state in which the electric wire 21 is bonded to the high-voltage terminal 11a. It is preferable that the tip portion 32 does not protrude from the high-voltage terminal 11a when the electric wire 21 is bonded to the high-voltage terminal 11a. The material and the thickness of the conductive section 23 and the material and the thickness of the insulating coating 24 are appropriately determined insofar as a voltage of 50 to 200 kV/cm can be applied. Examples of the material for the conductive section 23 can include nickel, copper, and the like. The shape of the cross section of the conductive section 23 in the direction perpendicular to the longitudinal direction of the conductive section 23 is not particularly limited, but is preferably a rectangle, a circle, an ellipse, or the like. It is preferable that the conductive section 23 have a cross-sectional area of 0.1 to 1.0 mm$^2$. Examples of the material for the insulating coating 24 include a mica glass tape, a silica yarn having a purity of 90% or more, a polyimide tape, and the like. The thickness of the insulating coating 24 is preferably 0.2 to 1.0 mm. The length of the electric wire 21 is preferably 15 to 30 cm.

In the particulate matter detection device 100 according to this embodiment, the takeout lead terminal of one electrode 12 of one of the pair of electrodes 11 and 12 is disposed at the other end 1b of the detection device body 1. The takeout lead terminal is electrically connected to the electrode disposed in the detection device body 1 of the particulate matter detection device 100, and is connected to a line from a power supply or the like used to externally apply a voltage to the electrode. The particulate matter detection device 100 includes a plurality of takeout lead terminals (takeout lead terminals 11a, 12a, 13a, and 14a) that are respectively connected to the pair of electrodes 11 and 12, the heating section 13, a ground electrode 14, and the like. In the particulate matter detection device 100 according to this embodiment shown in FIG. 1B, the takeout lead terminal 12a of the electrode 12 is disposed at the other end 1b of the detection device body 1. Since the distance between the area (i.e., one end 1a) in which the through-hole and the pair of electrodes are formed and the takeout lead terminal can be increased by disposing the takeout lead terminal of one of the pair of electrodes 11 and 12 at the other end 1b of the detection device body 1, only the end 1a on which the through-hole and the like are formed can be inserted into a pipe through which high-temperature exhaust gas flows, while allowing the other end 1b on which the takeout lead terminal 12a is disposed to be positioned outside the pipe. If the takeout lead terminal 12a is exposed to a high temperature, the particulate matter detection accuracy may decrease, it may be difficult to stably detect a particulate matter, or a contact failure between an electrical terminal and a harness used for external connection may occur during long-term use, so that the particulate matter may not be measured. Therefore, the particulate matter can be detected accurately and stably by allowing the takeout lead terminal 12a to be positioned outside the pipe so that the takeout lead terminal 12a is not exposed to a high temperature.

As shown in FIG. 1B, the takeout lead terminal 12a disposed at the other end 1b of the detection device body 1 is preferably disposed on the side surface of the other end 1b of the detection device body 1 to extend in the longitudinal direction. It is preferable that the takeout lead terminal 12a be disposed at one end of the side surface of the other end 1b of the detection device body 1 in the widthwise direction. In FIG. 1B, the other end 1b of the detection device body 1 can has a reduced width. Note that the other end 1b of the detection device body 1 may or may not have a reduced width. The shape and the size of the takeout lead terminal 12a are not particularly limited. For example, the takeout lead terminal 12a is preferably in the shape of a strip having a width of 0.1 to 2.0 mm and a length of 0.5 to 20 mm. Examples of the material for the takeout lead terminal 12a include Ni, Pt, Cr, W, Mo, Al, Au, Ag, Cu, and the like.

The takeout lead terminal (high-voltage terminal) 11a of the other electrode 11 of the pair of electrodes 11 and 12 is preferably disposed between one end 1a and the other end 1b of the detection device body 1. Therefore, the takeout lead terminal (takeout lead terminal 12a) of the electrode 12 and the takeout lead terminal (takeout lead terminal 11a) of the electrode 11 are disposed at an interval. This prevents a situation in which a creeping discharge occurs on the surface of the detection device body 1 when applying a voltage between the takeout lead terminal 11a and the takeout lead terminal 12a using the takeout lead terminal 11a as a high-voltage electrode in order to apply a voltage between the pair of electrodes 11 and 12. Note that the term "one end of the detection device body" used herein refers to an area of the detection device body 1 that corresponds to 30% of the total length of the detection device body 1 from one end face 1c of the detection device body 1. Note that the term "the other end of the detection device body" used herein refers to an area of the detection device body 1 that corresponds to 30% of the total length of the detection device body 1 from the other end face 1d of the detection device body 1. Therefore, the area between one end 1a and the other end 1b of the detection device body 1 refers to the area of the detection device body 1 other than one end 1a and the other end 1b. In the particulate matter detection device 100 according to this embodiment, the distance between the takeout lead terminal 11a and the takeout lead terminal 12a is preferably 5 to 100 mm, and more preferably 10 to 70 mm. If the distance between the takeout lead terminal 11a and the takeout lead terminal 12a is less than 5 mm, a short circuit due to a creeping discharge may occur. If the distance between the takeout lead terminal 11a and the takeout lead terminal 12a is more than 100 mm, when installing the detection device body 1 of the particulate matter detection device 100 in a pipe or the like so that the takeout lead terminal 11a is positioned outside the pipe, the detection device body 1 may protrude from the pipe to a large extent. This makes it difficult to install the detection device body 1 in a narrow space.

The distance between the through-hole 2 and the takeout lead terminal 11a disposed between one end 1a and the other end 1b of the detection device body 1 is preferably 10 mm or more, and more preferably 20 mm or more. If the distance between the through-hole 2 and the takeout lead terminal 11a is less than 10 mm, when installing the particulate matter detection device 100 in a pipe so that the through-hole 2 is inserted into the pipe, the takeout lead terminal 11a may be affected by the heat of high-temperature exhaust gas that passes through the pipe.

The shape and the size of the takeout lead terminal (high-voltage terminal) 11a are not particularly limited. For example, the takeout lead terminal 11a preferably has a polygonal such as quadrangular shape having a width of 0.5 to 3 mm and a length of 0.5 to 3 mm. Examples of the material for the takeout lead terminal 11a include Ni, Pt, Cr, W, Mo, Al, Au, Ag, Cu, stainless steel, kovar, and the like.

The particulate matter adsorbed on the wall surface of the through-hole is detected by measuring a change in electrical properties of the wall that defines the through-hole. Specifically, impedance calculated from the capacitance or the like between the pair of electrodes 11 and 12 is measured, and the mass of the particulate matter adsorbed on the wall surface of the through-hole is calculated from a change in impedance to detect the particulate matter contained in the exhaust gas, for example. Therefore, the particulate matter detection device 100 according to this embodiment preferably further includes a measurement section that is connected to the takeout lead terminals 11a and 12a and measures the impedance between the electrodes 11 and 12. Examples of the measurement section can include an LCR meter, an impedance analyzer, and the like that can measure impedance in addition to capacitance. Note that another pair of electrodes for measuring a change in electrical properties of the wall the defines the through-hole may be disposed in the through-hole, and the impedance between the other pair of electrodes may be measured instead of measuring the impedance between the electrodes 11 and 12.

In the particulate matter detection device 100 according to this embodiment, the detection device body 1 is formed to extend in one direction. The longitudinal length of the detection device body 1 is not particularly limited, but is preferable to have a length that allows a particulate matter contained in exhaust gas to be efficiently sampled when inserted into an exhaust gas pipe. In the particulate matter detection device 100 according to this embodiment, the through-hole 2 is formed at one end 1a of the detection device body 1 in the longitudinal direction. The thickness of the detection device body 1 (i.e., the dimension of the detection device body 1 in the direction perpendicular to both "the longitudinal direction of the detection device body" and "the gas circulation direction") is not particularly limited, but is preferably about 0.5 to 3 mm, for example. Note that the thickness of the detection device body 1 refers to the maximum thickness of the detection device body 1 in the thickness direction. The dimension of the detection device body 1 in the circulation direction in which gas passes through the through-hole 2 (i.e., the dimension of the detection device body 1 in the gas circulation direction) is not particularly limited, but is preferably about 2 to 20 mm, for example. The longitudinal length of the detection device body 1 is preferably larger than the thickness of the detection device body 1 by a factor of 10 to 100, and larger than the dimension of the detection device body 1 in the gas circulation direction by a factor of 3 to 100. As shown in FIGS. 1A and 1B, the detection device body 1 may be in the shape of a plate having a rectangular cross-sectional shape perpendicular to the longitudinal direction, or may be in the shape of a rod having a circular or elliptical cross-sectional shape perpendicular to the longitudinal direction, or may have another shape insofar as the detection device body 1 extends in one direction. The material for the detection device body 1 is preferably at least one compound selected from the group consisting of alumina, cordierite, mullite, glass, zirconia, magnesia, and titania. It is more preferable to use cordierite from the viewpoint of excellent thermal shock resistance. The electrodes 11 and 12 covered with a dielectric can be formed by burying the electrodes 11 and 12 in the detection device body 1 that is formed of such a dielectric. This ensures that the particulate matter detection device 100 exhibits excellent heat resistance, dielectric breakdown resistance, and the like. The term "dielectric" used herein refers to a substance in which dielectricity is predominant over conductivity and behaves as an insulator for a direct-current voltage.

In the particulate matter detection device 100 according to this embodiment, the pair of electrodes 11 and 12 are buried in the wall that defines the through-hole 2, as shown in FIG. 3. The pair of electrodes 11 and 12 that are covered with the dielectric are disposed on either side of the through-hole 2 sandwiched. Therefore, a discharge can occurs in the through-hole 2 by applying a given voltage between the electrodes 11 and 12. The particulate matter detection device 100 necessary has at least one pair of electrodes, and may have two or more pairs of electrodes. The electrodes are buried in the wall that defines the through-hole 2, and are preferably disposed on either side of the through-hole 2 as shown in FIG. 3. Note that the pair of electrodes may be disposed at arbitrary positions in the wall that defines the through-hole 2 insofar as the electrical properties of the wall can be detected and a discharge occurs in the through-hole 2. A plurality of pairs of electrodes may be disposed, and a discharge and electrical property detection may be separately performed using different pairs of electrodes. The type of discharge is preferably selected from the group consisting of a silent discharge, a streamer discharge, and a corona discharge. In order to cause such a discharge, the particulate matter detection device 100 according to this embodiment preferably further includes a discharge power supply that is connected to the takeout lead terminals 11a and 12a. The discharge power supply is preferably a high-voltage alternating-current power supply or direct-current power supply, for example. A pulse voltage, an alternating-current voltage (e.g., rectangular wave), or the like is preferably applied when causing a discharge to occur. The applied voltage is preferably 50 to 200 kV/cm, although the applied voltage may vary depending on the gap between the pair of electrodes and the exhaust gas temperature. The power supplied when applying a voltage is preferably 0.1 to 10 W.

When the particulate matter contained in a fluid that flows into the through-hole 2 is not charged, the particulate matter detection device 100 according to this embodiment causes a discharge to occur in the through-hole 2 so that the particulate matter is charged and electrically adsorbed on the wall surface of the through-hole 2. When the particulate matter contained in a fluid that flows into the through-hole 2 has already been charged, the particulate matter need not necessarily be charged by causing a discharge to occur in the through-hole 2. Specifically, the charged particulate matter is electrically adsorbed on the wall surface of the through-hole 2 without causing a discharge to occur in the through-hole 2. When charging the particulate matter by causing a discharge to occur in the through-hole 2, the charged particulate matter is electrically drawn to the electrode that has a polarity opposite to that of the charged particulate matter during a discharge, and adsorbed on the wall surface of the through-hole 2. On the other hand, when the particulate matter has already been charged before the particulate matter flows into the through-hole 2, the charged particulate matter is electrically drawn to the electrode that has a polarity opposite to that of the charged particulate matter by applying a given voltage between the electrodes 11 and 12. When the particulate matter has already been charged before the particulate matter flows into the through-hole 2, the voltage applied between the electrodes 11 and 12 is preferably 4 to 40 kV/cm.

The shape and the size of the electrodes 11 and 12 are not particularly limited insofar as a discharge occurs in the through-hole 2. For example, the electrodes 11 and 12 may have a rectangular shape, a circular shape, an elliptical shape, or the like. The electrodes 11 and 12 preferably have a size equal to or larger than 70% of the area of the through-hole 2 when viewed from the side surface.

The thickness of the electrodes 11 and 12 is not particularly limited insofar as a discharge occurs in the through-hole 2. The thickness of the electrodes 11 and 12 is preferably 5 to 30 μm, for example. Examples of the material for the electrodes 11 and 12 include Pt, Mo, W, and the like.

The distance between one (electrode 11) of the pair of electrodes and the through-hole 2 and the distance between the other (electrode 12) of the pair of electrodes and the through-hole 2 is preferably 50 to 500 μm, and more preferably 100 to 300 μm. This ensures that a discharge effectively occurs in the through-hole. The distance between the electrode 11 and the through-hole 2 and the distance between the electrode 12 and the through-hole 2 mean the thickness of the dielectric that covers the electrode 11 and the electrode 12 in the area that faces the through-hole 2.

Figure 6:
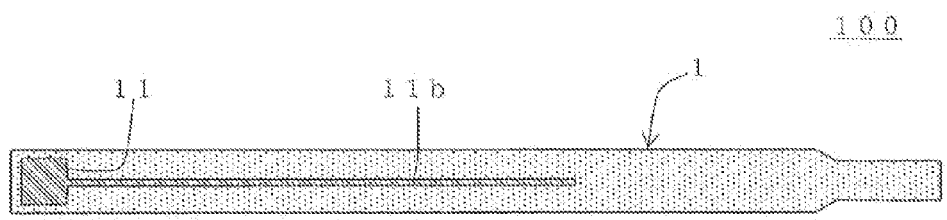
FIG. 6 is a schematic view showing a cross section cut along B-B' line of the particulate matter detection device according to one embodiment of the present invention shown in FIG. 3.
Figure 7:
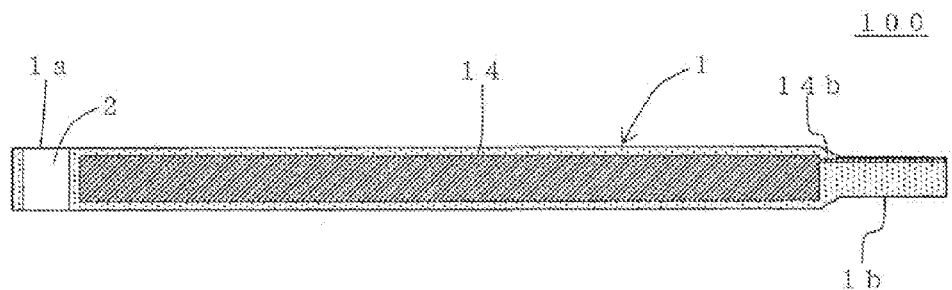
FIG. 7 is a schematic view showing a cross section cut along C-C' line of the particulate matter detection device according to one embodiment of the present invention shown in FIG. 3.

As shown in FIG. 6, in the particulate matter detection device 100 according to this embodiment, the line 11b that extends in the longitudinal direction of the detection device body 1 is connected to the electrode 11. The line 11b is via-connected to the takeout lead terminal 11a shown in FIG. 1B at its tip portion (i.e., the tip portion that is not connected to the electrode 11). As shown in FIG. 7, the through-hole 2 is formed at one end 1a of the detection device body 1. FIG. 6 is a schematic view showing a cross section cut along B-B' line of the particulate matter detection device according to one embodiment of the present invention shown in FIG. 3, and FIG. 7 is a schematic view showing a cross section cut along C-C' line of the particulate matter detection device according to one embodiment of the present invention shown in FIG. 3.

Figure 8:
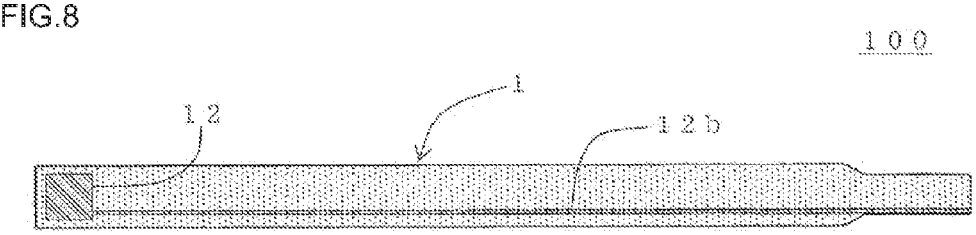
FIG. 8 is a schematic view showing a cross section cut along D-D' line of the particulate matter detection device according to one embodiment of the present invention shown in FIG. 3.

As shown in FIG. 8, the line 12b that extends in the longitudinal direction of the detection device body 1 is connected to the electrode 12. The line 12b is via-connected to the takeout lead terminal 12a shown in FIG. 1B. FIG. 8 is a schematic view showing a cross section cut along D-D' line of the particulate matter detection device according to one embodiment of the present invention shown in FIG. 3.

The width of the lines 11b and 12b is not particularly limited, but is preferably about 0.2 to 1 mm, for example. The thickness of the lines 11b and 12b is not particularly limited, but is preferably about 5 to 30 μm, for example. Examples of the material for the lines 11b and 12b include Pt, Mo, W, and the like.

As shown in FIGS. 3 and 6 to 8, in the particulate matter detection device 100 according to this embodiment, the ground electrode 14 in the shape of a strip is preferably disposed between the lines 11b and 12b that respectively extend from the pair of electrodes 11 and 12. The ground electrode refers to an electrode that is grounded. The ground electrode 14 is preferably disposed so that a current does not flow from one (e.g., line 11b) of the lines 11b and 12b to the other line (e.g., line 12b). When vertically moving and superimposing at least one of the lines 11b and 12b on the ground electrode 14, it is preferable that 95% of the line overlaps the ground electrode 14 in the lengthwise direction. It is preferable that the ground electrode 14 be disposed in a plane parallel to the longitudinal direction and the widthwise direction of the detection device body 1. It is preferable that the width of the ground electrode 14 be 70 to 95% of the width of the detection device body 1, and the length of the ground electrode 14 be 50 to 95% of the length of the detection device body 1. It is more preferable that the width of the ground electrode 14 be 80 to 90% of the width of the detection device body 1, and the length of the ground electrode 14 be 70 to 90% of the length of the detection device body 1. This makes it possible to more effectively prevent a situation in which a current flows from one line to the other line. The "width of the ground electrode 14" refers to the dimension of the ground electrode 14 in the extension direction of the through-hole 2 (fluid circulation direction), and the "width of the detection device body 1" refers to the dimension of the detection device body 1 in the extension direction of the through-hole 2 (fluid circulation direction). As shown in FIG. 4, the through-hole 2 is formed at one end 1a of the detection device body 1, and the ground electrode 14 that extends in the shape of a strip from the through-hole 2 toward the other end 1b is buried in the detection device body 1.

The particulate matter detection device according to this embodiment measures a change in electrical properties of the wall that defines the through-hole by detecting given electrical properties between the pair of electrodes to detect particulate matter adsorbed on the wall surface of the through-hole. When detecting given electrical properties between the pair of electrodes, the particulate matter detection device also detects the given electrical properties between the two lines that are connected to the pair of electrodes and buried in the dielectric. That is, values detected by the pair of electrodes and the two lines are obtained as the measured values. When the effects of the given electrical properties between the two lines are great, the electrical properties of the wall that defines the through-hole changes. In this case, even if the change in electrical properties of the wall that defines the through-hole is detected by the pair of electrodes, the electrical properties between the two lines connected to the pair of electrodes are also measured. In this case, there is a problem that this may make it difficult to accurately measure a change in electrical properties of the wall that defines the through-hole. However, since the particulate matter detection device according to this embodiment can detect the electrical properties between the pair of electrodes while suppressing the effects of the lines that extend from the pair of electrodes using the ground electrode, a measurement error due to the lines can be eliminated. This makes it possible to accurately measure a change in electrical properties of the wall that defines the through-hole.

Note that the ground electrode does not have to be included in the particulate matter detection device, but when the ground electrode is not included therein, a current flows through the dielectric placed between the two lines from the line connected to one of the pair of electrodes to the line connected to the other of the pair of electrodes so that the electrical properties between the two lines is detected. On the other hand, since the particulate matter detection device according to this embodiment includes the ground electrode between the two lines, a current flows from one line to the ground electrode, but does not flow to the other line. Therefore, the electrical properties between the two lines are not detected. When applying a voltage between the pair of electrodes, only the electrical properties of the wall that defines the through-hole positioned between the pair of electrodes can be detected.

The shape of the ground electrode 14 is not particularly limited. The ground electrode 14 may have a rectangular shape, an elliptical shape, or the like. The thickness of the ground electrode 14 is not particularly limited insofar as a current does not flow from one line to the other line. The thickness of the ground electrode 14 is preferably 10 to 200 μm, for example. Examples of the material for the ground electrode 14 include Ni, Pt, Cr, W, Mo, Al, Au, Ag, Cu, stainless steel, kovar, and the like.

The distance between the ground electrode 14 and the line 11b and the distance between the ground electrode 14 and the line 12b are preferably 100 to 500 μm, and more preferably 150 to 250 µm. This makes it possible to more effectively prevent a situation in which a current flows from one line to the other line.

In the particulate matter detection device 100 according to this embodiment, the line 14b that extends in the longitudinal direction of the detection device body 1 is connected to the ground electrode 14. The line 14b is via-connected to the takeout lead terminal 14a shown in FIG. 1B at its tip portion (i.e., the tip portion that is not connected to the ground electrode 14).

The width of the line 14b is not particularly limited, but is preferably about 0.2 to 1 mm, for example. The thickness of the line 14b is not particularly limited, but is preferably about 5 to 30 µm, for example. Examples of the material for the line 14b include Pt, Mo, W, and the like.

Figure 9:
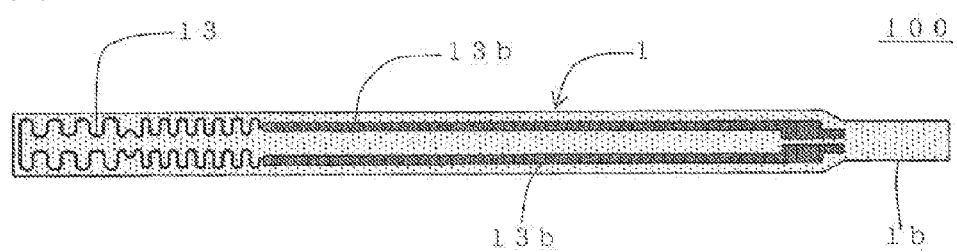
FIG. 9 is a schematic view showing a cross section cut along E-E' line of the particulate matter detection device according to one embodiment of the present invention shown in FIG. 3.
Figure 10A:
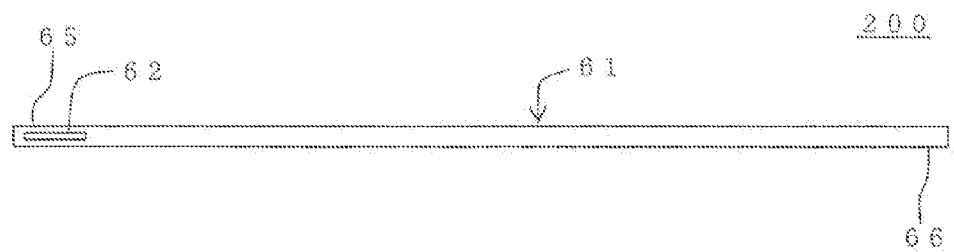
FIG. 10A is a front view schematically showing a particulate matter detection device.
Figure 10B:
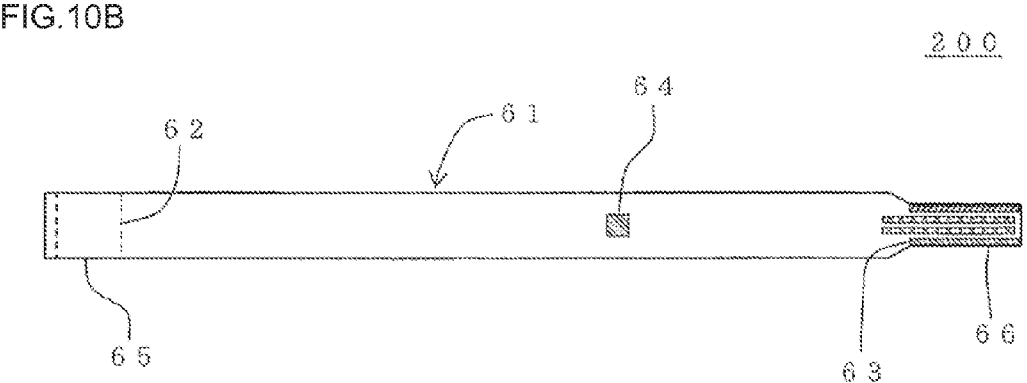
FIG. 10B is a side view schematically showing a particulate matter detection device.

As shown in FIGS. 3 and 9, the particulate matter detection device 100 according to this embodiment preferably further includes the heating section 13 that is disposed (buried) in the detection device body 1 along the wall surface (i.e., the wall surface that is parallel to the side surface of the detection device body 1) of the through-hole 2. The particulate matter adsorbed on the electrode can be heated and oxidized by the heating section 13. Moreover, the temperature of the inner space of the through-hole 2 can be adjusted to a desired temperature when measuring the mass of particulate matter, for example, so that a change in electrical properties of the wall that defines the through-hole 2 can be stably measured. The heating section 13 may be in the shape of a wide film. As shown in FIG. 9, it is preferable that the heating section 13 be formed by disposing a linear metal material in a wave-like manner and turning the metal material in the shape of the letter U at the tip portion. This makes it possible to uniformly heat the inner space of the through-hole. Examples of the material for the heating section 13 include Pt, Mo, W, and the like. The heating section 13 is preferably buried in the detection device body 1 along the wall surface of the through-hole 2. As shown in FIG. 7, the heating section 13 may be formed to extend toward the other end 1b of the detection device body 1 from the position at which the through-hole 2 is formed. This reduces the difference in temperature between the inside of the through-hole and the vicinity of the through-hole so that the element rarely breaks even if the element is rapidly heated. It is preferable that the heating section 13 increase the temperature of the inner space of the through-hole 2 up to 650° C. FIG. 9 is a schematic view showing a cross section cut along E-E' line of the particulate matter detection device according to one embodiment of the present invention shown in FIG. 3.

In the particulate matter detection device 100 according to this embodiment, it is preferable that at least one heating section 13 be disposed on the side of at least one of the pair of electrodes 11 and 12 opposite to the side on which the through-hole is formed. In the particulate matter detection device 100 according to this embodiment shown in FIG. 3, the heating section 13 is disposed on the side of the electrode 12 opposite to the side that faces the through-hole 2. If the heating section 13 is disposed on the side of at least one of the pair of electrodes 11 and 12 opposite to the side that faces the through-hole, a change in electrical properties of the wall that defines the through-hole 2 can be easily measured by the pair of electrodes 11 and 12 without being affected by the heating section 13. In FIG. 3, one heating section 13 is provided. Note that a plurality of heating sections 13 may be disposed on the side of the electrode 12 opposite to the side that faces the through-hole 2. In FIG. 3, the heating section 13 is disposed on the side of at least one (electrode 12) of the pair of electrodes 11 and 12 opposite to the side that faces the through-hole 2. Note that it is also preferable that at least one heating section 13 be disposed on the side of each of the pair of electrodes 11 and 12 opposite to the side that faces the through-hole 2. An arbitrary number of heating sections 13 may be disposed in an arbitrary arrangement in order to appropriately adjust the temperature and oxidize and remove the collected particulate matter.

As shown in FIG. 9, the heating section 13 is connected to lines 13b, 13b. The lines 13b, 13b are respectively via-connected to the takeout lead terminals 13a,13a shown in FIG. 1B. The takeout lead terminal 13a of the heating section 13 is preferably disposed at the other end 1b of the detection device body 1 in the same manner as the takeout lead terminals 11a and 12a of the electrodes 11 and 12 in order to avoid the effects of heat when one end 1a of the detection device body 1 is heated. In FIG. 1B, the takeout lead terminal 12a is disposed at one edge of the side surface of the detection device body 1 in the widthwise direction, and the takeout lead terminals 13a, 13a are disposed in two rows side by side adjacent to the takeout lead terminal 12a. Note that the arrangement of the takeout lead terminal 12a and the takeout lead terminals 13a, 13a is not limited thereto.

When the heating section 13 is linear, the width of the heating section 13 is preferably about 0.05 to 1 mm, for example. The thickness of the heating section 13 is not particularly limited, but is preferably about 5 to 30 µm, for example. The width of the line 13b is not particularly limited, but is preferably about 0.7 to 4 mm, for example. The thickness of the line 13b is not particularly limited, but is preferably about 5 to 30 µm, for example. The width of the takeout lead terminal 13a connected to the heating section 13 is not particularly limited, but is preferably about 0.1 to 2 mm, for example. The thickness of the takeout lead terminal 13a is not particularly limited, but is preferably about 5 to 1000 µm, for example. Examples of the material for the line 13b and the takeout lead terminal 13a include Ni, Pt, Cr, W, Mo, Al, Au, Ag, Cu, stainless steel, kovar, and the like.

The particulate matter detection device 100 according to this embodiment may be configured to oxidize and remove a particulate matter adsorbed on the electrode by applying a voltage between the pair of electrodes 11 and 12 so that a discharge occurs in the through-hole 2. When oxidizing and removing the particulate matter by causing a discharge to occur in the through-hole 2, the field intensity is preferably 10 to 200 kV/cm, and the amount of energy supplied is 0.05 to 10 J/µg with respect to the treatment target substance.

The particulate matter detection device 100 according to this embodiment preferably further includes a heating power supply that is connected to the takeout lead terminal 13a of the heating section 13. The heating power supply may be a constant current power supply or the like.

In the particulate matter detection device 100 according to this embodiment, the shape and the size of the through-hole 2 are not particularly limited insofar as exhaust gas passes through the through-hole 2 and the amount of particulate matter can be measured. The dimension of the through-hole 2 in the longitudinal direction of the detection device body is preferably about 2 to 20 mm. The width of the area of the through-hole 2 positioned between the electrodes 11 and 12 (i.e., the dimension of the through-hole 2 in the direction perpendicular to the longitudinal direction of the detection device body and the gas circulation direction) is preferably about 0.3 to 3 mm. If the through-hole 2 has dimensions within the above range, exhaust gas containing a particulate matter can sufficiently pass through the through-hole 2. Moreover, it is possible to cause a discharge effective for charging the particulate matter to occur in the through-hole 2.

In the particulate matter detection device 100 according to this embodiment, it is preferable that the detection device body 1 be formed by stacking a plurality of tape-shaped ceramic (ceramic sheets). In this case, since the particulate matter detection device 100 can be formed by stacking a plurality of tape-shaped ceramic while interposing the electrodes, the line, and the like between the tape-shaped ceramic, the particulate matter detection device 100 according to this embodiment can be efficiently produced.

The particulate matter detection device 100 according to this embodiment is particularly effective when a particulate matter that passes through the through-hole 2 is soot discharged from a diesel engine.

A method of producing the particulate matter detection device 100 according to this embodiment is described below.
(Preparation of Forming Raw Material)

At least one ceramic raw material (dielectric raw material) selected from the group consisting of alumina, a cordierite-forming raw material, mullite, glass, zirconia, magnesia, and titania and other components used as a forming raw material are mixed to prepare a slurried forming raw material. The above raw material is preferable as the ceramic raw material (dielectric raw material). Note that the ceramic raw material is not limited thereto. As the components other than the ceramic raw material, it is preferable to use a binder, a plasticizer, a dispersant, a dispersion medium, and the like.

The binder is not particularly limited. An aqueous binder or a non-aqueous binder may be used. As the aqueous binder, methyl cellulose, polyvinyl alcohol, polyethylene oxide, or the like may be suitably used. As the non-aqueous binder, polyvinyl butyral, an acrylic resin, polyethylene, polypropylene, or the like may be suitably used. Examples of the acrylic resin include a (meth)acrylic resin, a (meth)acrylate copolymer, an acrylate-methacrylate copolymer, and the like.

The binder is preferably added in an amount of 3 to 20 parts by mass, and more preferably 6 to 17 parts by mass, with respect to 100 parts by mass of the dielectric raw material. If the amount of the binder is within the above range, cracks or the like do not occur when forming the slurried forming raw material into a green sheet, or when drying and firing the green sheet.

As the plasticizer, glycerol, polyethylene glycol, dibutyl phthalate, di(2-ethylhexyl)phthalate, diisononyl phthalate, or the like may be used.

The plasticizer is preferably added in an amount of 30 to 70 parts by mass, and more preferably 45 to 55 parts by mass, with respect to 100 parts by mass of the binder. If the amount of the plasticizer is more than 70 parts by mass, the resulting green sheet becomes too soft and may be deformed when processing the green sheet. If the amount of the plasticizer is less than 30 parts by mass, the resulting green sheet becomes too hard so that the handling capability may deteriorate. As a result, racks may occur when merely bending the green sheet).

As the dispersant, an aqueous dispersant such as anionic surfactant, wax emulsion, or pyridine or a non-aqueous dispersant such as fatty acid, phosphate, or synthetic surfactant) may be used.

The dispersant is preferably added in an amount of 0.5 to 3 parts by mass, and more preferably 1 to 2 parts by mass, with respect to 100 parts by mass of the dielectric raw material. If the amount of the dispersant is less than 0.5 parts by mass, the dispersibility of the dielectric raw material may decrease. As a result, the green sheet may produce cracks or the like. If the amount of the dispersant is more than 3 parts by mass, the amount of impurities may increase during firing although the dispersibility of the dielectric raw material remains the same.

As the dispersion medium, water or the like may be used. The dispersion medium is preferably added in an amount of 50 to 200 parts by mass, and more preferably 75 to 150 parts by mass, with respect to 100 parts by mass of the dielectric raw material.

The above materials are sufficiently mixed using an alumina pot and alumina cobblestone to prepare a slurried forming raw material for forming a green sheet. The slurried forming raw material may be prepared by mixing the materials by ball milling using a mono ball.

The resulting slurried forming raw material is stirred under reduced pressure to remove bubbles, and the viscosity of the slurried forming raw material is adjusted to a given value. The viscosity of the slurried forming raw material thus prepared is preferably 2.0 to 6.0 Pa·s, more preferably 3.0 to 5.0 Pa·s, and particularly preferably 3.5 to 4.5 Pa·s. The slurry can be easily formed into a sheet by adjusting the viscosity of the slurry to a value within the above range. It may be difficult to form the slurry into a sheet if the viscosity of the slurry is too high or too low. The viscosity of the slurry refers to a value measured using a Brookfield viscometer.
(Forming Process)

The slurried forming raw material obtained by the above method is formed into a tape to obtain a green sheet that extends in one direction. The forming process method is not particularly limited insofar as a green sheet can be formed by forming the forming raw material into a sheet. The conventional methods such as a doctor blade method, a press forming method, a rolling method, a calendar roll method, or the like may be used. A green sheet for forming a through-hole is produced so that a through-hole is formed when stacking the green sheets.

The thickness of the green sheet is preferably 50 to 800 µm.

An electrode, a line, a heating section, and a takeout lead terminal are formed on the surface of the resulting green sheet. For example, when producing the particulate matter detection device 100 as shown in FIGS. 1A, 1B, and 2, an electrode, a line, a heating section, and a takeout lead terminal are printed on the green sheet at corresponding positions so that an electrode, a line, a heating section, and a takeout lead terminal are formed at given positions as shown in FIGS. 1B and 4 to 7. A conductive paste for forming an electrode, a line, a heating section, and a takeout lead terminal is prepared. The conductive paste may be prepared by adding a binder and a solvent such as terpineol to a powder that contains at least one component selected from the group consisting of gold, silver, platinum, nickel, molybdenum, and tungsten depending on the materials necessary for forming the electrode, line, etc., and sufficiently kneading the mixture using a triple roll mill or the like. Each conductive paste that contains a material necessary for forming an electrode, line, etc. is printed on the surface of the green sheet by screen printing or the like to form an electrode, a line, a heating section, and a takeout lead terminal having a given shape.

More specifically, a plurality of green sheets are produced. An electrode is formed at one end of one side of each of two of the green sheets, and a line that extends from the electrode to the other end is formed to obtain two electrode green sheets. A ground electrode is formed on another green sheet at a position at which the ground electrode overlaps the line when stacked on the electrode green sheet to obtain a ground electrode green sheet. Furthermore, a cut area which forms a through-hole is formed in another green sheet or the ground electrode green sheet at a position at which the cut area overlaps the electrode when stacked on the electrode green sheet to obtain a cut area green sheet. When forming a cut area in the ground electrode green sheet, the ground electrode green sheet is the same as the cut area green sheet. When forming a cut area in the ground electrode green sheet, the ground electrode may be formed after forming the cut area. A green sheet on which an electrode and the like were not formed is stacked on each of the electrode green sheets to cover the electrode and the line with the green sheet to obtain electrode-buried green sheets. The ground electrode green sheet and the cut area green sheet are sandwiched between the electrode-buried green sheets to obtain a green sheet laminate in which the cut area is interposed between the two electrodes and the ground electrode is interposed between the two lines. The green sheets may be stacked at the same time, or the electrode-buried green sheet may be produced first, and stacked on another green sheet. The green sheets are preferably stacked under pressure.

According to the method of producing the particulate matter detection device according to the present invention, since the desired electrode and the like are disposed on a plurality of green sheets, and the green sheets in which the electrode and the like are formed are stacked, dried, and fired to produce a particulate matter detection device, the particulate matter detection device according to the present invention can be efficiently produced.

(Firing)

The green sheet laminate is dried and fired to obtain a particulate matter detection device. Specifically, the green sheet laminate is dried at 60 to 150° C., and fired at 1200 to 1600° C. to obtain a particulate matter detection device. When the green sheet contains an organic binder, the green sheet is preferably debinded at 400 to 800° C. before firing.

(Bonding High-Voltage Terminal to Electric Wire)

An insulating coating at the tip portion of a given electric wire is removed. A metal plate that is made of a given material and formed in the shape of the letter "T" is preferably used as the electric wire securing member. The tip portion of the electric wire is placed on the T-shaped metal plate, and each end of the wing area of the T-shaped metal plate is preferably bent to sandwich the end of the electric wire, folding back. The tip portion of the electric wire is preferably placed on the T-shaped metal plate so that the tip portion of the electric wire perpendicularly intersects the longitudinal direction of the wing area of the metal plate, and is disposed at the center of the wing area such that the end of the electric wire is positioned in the body area.

It is preferable to braze a given bonding metal plate to the surface of the high-voltage terminal. The bonding metal plate is preferably brazed as follows. First, the surface of the matrix is cleaned in order to improve the wettability of the filler metal, and flux is applied to the bonding surface in order to prevent oxidation of the surface of the matrix due to heating, and promote the flow of the filler metal. After assembling and heating the members, the filler metal is melted at the joint and spread over the entire bonding surface. Then, the members are then slowly cooled. After the members have been joined, a residue of the flux is optionally removed. The product is then cleaned to remove an oxide film formed by heating to complete brazing. It is preferable to braze the bonding metal plate to the high-voltage terminal since it is possible to select a metal plate material that has a coefficient of thermal expansion similar to that of the high-voltage terminal. The electric wire securing member on which the electric wire is secured is preferably welded to the surface of the bonding metal plate to obtain the particulate matter detection device according to this embodiment. The electric wire securing member is preferably spot-welded to the bonding metal plate. It is preferable to weld the electric wire securing member to the bonding metal plate since the bonding strength can be improved.

EXAMPLES

The present invention is further described below by way of examples. Note that the present invention is not limited to the following examples.

Example 1

Preparation of Forming Raw Material

An alumina pot was charged with alumina as dielectric raw material, polyvinyl butyral as binder, di(2-ethylhexyl) phthalate as plasticizer, sorbitan trioleate as dispersant, and an organic solvent (xylene:butanol=6:4 (mass ratio)) as dispersion medium. The components were mixed to prepare a slurried forming raw material for forming a green sheet. 7 parts by mass of the binder, 3.5 parts by mass of the plasticizer, 1.5 parts by mass of the dispersant, with respect to 100 parts by mass of the organic solvent were used with respect to 100 parts by mass of alumina.

The slurried forming raw material thus obtained was stirred under reduced pressure to remove bubbles, and the viscosity of the slurried forming raw material was adjusted to 4 Pa·s. The viscosity of the slurry was measured using a Brookfield viscometer.

(Forming Process)

Next, the slurried forming raw material obtained by the above method was formed into a sheet using a doctor blade method. At this time, the cut area green sheet was also produced so that a through-hole was formed when stacking the green sheets. The thickness of the green sheet was 250 μm.

An electrode, a ground electrode, a heating section, a line, and a takeout lead terminal as shown in FIGS. 1B and 4 to 7 were formed on the surface of the resulting green sheet. A conductive paste for forming the electrode, ground electrode, line, and takeout lead terminal to be disposed was prepared by adding 2-ethylhexanol as solvent, polyvinyl butyral as binder, di(2-ethylhexyl)phthalate (plasticizer), sorbitan trioleate as dispersant, alumina as green sheet common material, and a glass frit as sintering aid to a platinum powder, and sufficiently kneading the mixture using a kneader and a triple roll mill (platinum:alumina:glass frit:2-ethylhexanol:polyvinyl butyral:di(2-ethylhexyl)phthalate:sorbitan trioleate=80:15:5:50:7:3.5:1 (mass ratio)). A conductive paste for forming the heating section was prepared by adding 2-ethylhexanol (solvent), polyvinyl butyral as binder, di(2-ethylhexyl) phthalate as plasticizer, sorbitan trioleate as dispersant, alumina as green sheet common material, and a glass frit as sintering aid to a platinum powder, and sufficiently kneading the mixture using a kneader and a triple roll mill (platinum:alumina:glass frit:2-ethylhexanol:polyvinyl butyral:di(2-ethylhexyl)phthalate:sorbitan trioleate=80:15:5:50:7:3.5:1 (mass ratio)). The conductive paste thus prepared was printed on the surface of the green sheet by screen printing to form an electrode and the like having a given shape. Specifically, an electrode was formed at one end of one side of each of two green sheets, and a line that extends from the electrode to the other end was formed to obtain two electrode green sheets. A ground electrode was formed on another green sheet at a position at which the ground electrode overlaps the line when stacked on the electrode green sheet to obtain a ground electrode green sheet. A cut area which defines a through-hole was formed in another green sheet at a position at which the cut area overlaps the electrode when stacked on the electrode green sheet to obtain a cut area green sheet. A heating section was formed on another green sheet at a position at which the heating section overlaps the cut area (through-hole) when stacked on the cut area green sheet. A line extending from the heating section to the other end was formed to obtain a heating section green sheet. A green sheet on which an electrode and the like were not formed was stacked on each of the electrode green sheets to cover the electrode and the line with the green sheet to obtain electrode-buried green sheets. The ground electrode green sheet and the cut area green sheet were interposed between the electrode-buried green sheets. The heating section green sheet was then stacked on the electrode-buried green sheet to obtain a green sheet laminate in which the cut area was interposed between the two electrodes and the ground electrode was interposed between the two lines. The line and the takeout lead terminal were via-connected using a conductive paste.

The green sheets were stacked under pressure using a heating-type uniaxial press machine to obtain an unfired body as green sheet laminate of a particulate matter detection device.
(Firing)

The green sheet laminate (unfired body of particulate matter detection device) thus obtained was dried at 120° C., and fired at 1500° C. to obtain a particulate matter detection device. The resulting particulate matter detection device was in the shape of a rectangular parallelepiped of 0.7 cm×0.2 cm×12 cm. The other end of the particulate matter detection device had a reduced thickness as shown in FIG. 1B. The other end of the particulate matter detection device had a width of 4.25 cm and a reduced length of 1.2 cm. The cross-sectional shape of the through-hole in the direction perpendicular to the exhaust gas circulation direction was rectangular of 0.75 mm×5.0 mm. The high-voltage terminal had a rectangular shape of 2.0 mm×3.0 mm.
(Bonding to Electric Wire)

A T-shaped metal plate was used as an electric wire securing member. The tip portion of the electric wire was placed on the T-shaped metal plate, and each end of the wing area of the T-shaped metal plate was bent to secure the tip portion of the electric wire using the electric wire securing member. A structure shown in FIGS. 2A and 2B in which the tip portion 32 is secured using the electric wire securing member 31 was thus obtained. The T-shaped metal plate was bent using a tool such as pliers. The T-shaped metal plate had a wing area of 4.8 mm×1.0 mm and a body area of 7.0 mm×2.0 mm. As for the T-shaped metal plate, the longitudinal direction of the wing area was perpendicular to the longitudinal direction of the body area. The T-shaped metal plate was formed of stainless steel. The T-shaped metal plate had a thickness of 0.1 mm. The electric wire bonded to the high-voltage terminal had a structure in which a conductive section having a circular cross section in the direction perpendicular to the longitudinal direction was covered with an insulating coating having a thickness of 0.7 mm. The conductive section had a cross-sectional area of 0.3 mm². The conductive section was formed of nickel. The insulating coating was formed of a mica glass tape and a silica yarn having a purity of 90% or more.

A bonding metal plate was brazed to the high-voltage terminal. The bonding metal plate was brazed as follows. After cleaning the surface of the matrix, flux was applied to the bonding surface. After assembling and heating the members, a filler metal was melted at the joint and spread over the entire bonding surface. After the members were joined, a residue of the flux was removed. As the bonding metal plate, a metal plate having dimensions of 2.0 mm×3.0 mm was used. The bonding metal plate had a thickness of 0.1 mm. The bonding metal plate was formed of kovar.

The electric wire securing member on which the electric wire was secured was spot-welded to the bonding metal plate, and the electric wire was bonded to the high-voltage terminal to obtain a particulate matter detection device (Example 1). The electric wire was bonded to the high-voltage terminal as shown in FIGS. 2A and 2B (see the joint 22 between the electric wire 21 and the high-voltage terminal 11a). As a discharge power supply, a pulse power supply and a DC power supply were connected to the takeout lead terminals of the electrodes. An impedance analyzer (manufactured by Agilent Technologies) was used as a measurement section that measures the impedance between the electrodes. The measurement section was connected to the takeout lead terminals of the electrodes. The takeout lead terminal of the ground electrode was grounded. The bonding state of the electric wire and the high-voltage terminal of the particulate matter detection device thus obtained was inspected by the following method, and the amount of particulate matter was measured using the particulate matter detection device. The results are shown in Table 1.
(Bonding State Inspection Method)

A voltage of 2 kV was applied to the high-voltage electrode 11 from the electric wire through the high-voltage terminal 11a, and whether or not a discharge occurred in the through-hole formed in the detection device body was observed with the naked eye in a darkroom to determine whether or not the electric wire and the high-voltage terminal were electrically connected. A case where occurrence of a discharge was observed was evaluated as "Good", indicating good bonding state (electrical connection), and a case where occurrence of a discharge was not observed was evaluated as "Bad", indicating bad bonding state (electrical connection).
(Particulate Matter Measurement Method)

The resulting particulate matter detection device was installed in an exhaust pipe connected to a diesel engine. A direct-injection diesel engine of displacement: 2000 cc was used as the diesel engine. Exhaust gas was discharged at an engine speed of 1500 rpm, a torque of 24 N·m, an exhaust gas recirculation (EGR) rate of 50%, an exhaust gas temperature of 200° C., and an air intake of 1.3 m³/min (room temperature). The amount of particulate matter contained in the exhaust gas measured by a smoke meter ("4158" manufactured by AVL) was 2.0 mg/m³. The particulate matter was detected as follows. Before charging and collecting a particulate matter, the initial capacitance (pF) between the pair of electrodes was measured for one minute six times in a state in which exhaust gas was discharged from the diesel engine. After charging and collecting the particulate matter for one minute under the above conditions, the charging/collection operation was stopped. The capacitance (pF) (capacitance between the pair of electrodes after collecting the particulate matter for one minute) was measured for one minute six times. The average value of the six measured values was calculated for each of the initial capacitance and the capacitance after collecting the particulate matter for one minute. The mass of the collected particulate matter was calculated from the difference between the initial capacitance and the capacitance after collecting the particulate matter for one minute. A calibration curve was provided in advance for a change in capacitance with respect to the adsorption amount of particulate matter, and the mass of the collected particulate matter was calculated using the calibration curve. Note that the particulate matter was not burnt using a heater during the measurement. When charging and collecting the particulate matter, a DC voltage of 2.0 kV was applied using a high-voltage power supply. The capacitance between the electrodes was measured at an applied voltage (AC) of 2 V and a frequency of 10 kHz. The results are shown in Table 1.

TABLE 1

| | Bonding state | Capacitance | |
|---|---|---|---|
| Example 1 | Discharge was observed Electrical connection was good | Initial After collecting particulate matter for one minute | 1.08 1.78 |
| Example 2 | Discharge was observed Electrical connection was good | Initial After collecting particulate matter for one minute | 1.11 1.81 |
| Example 3 | Discharge was observed Electrical connection was good | Initial After collecting particulate matter for one minute | 1.12 1.83 |
| Comparative Example 1 | Discharge was not observed Electrical connection was poor | Initial After collecting particulate matter for one minute | 1.08 1.09 |

Example 2

A particulate matter detection device was produced in the same manner as in Example 1, except that the electric wire securing member on which the electric wire was secured was bonded to the high-voltage terminal through a conductive adhesive. As the conductive adhesive, a ceramic adhesive containing a metal powder such as nickel or aluminum was used. The bonding state of the electric wire and the high-voltage terminal of the particulate matter detection device was inspected by the above method, and the amount of particulate matter was measured using the particulate matter detection device. The results are shown in Table 1.

Example 3

A particulate matter detection device was produced in the same manner as in Example 1, except that the electric wire was bonded to the high-voltage terminal through a metal paste. As the metal paste, a silver paste was used. The bonding state of the electric wire and the high-voltage terminal of the particulate matter detection device was inspected by the above method, and the amount of particulate matter was measured using the particulate matter detection device. The results are shown in Table 1.

Comparative Example 1

A particulate matter detection device was produced in the same manner as in Example 1, except that the electric wire was bonded to the high-voltage terminal by soldering. The bonding state of the electric wire and the high-voltage terminal of the particulate matter detection device was inspected by the above method, and the amount of particulate matter was measured using the particulate matter detection device. The results are shown in Table 1.

As shown in Table 1, the particulate matter detection device of Example 1 most reliably prevented separation of the electric wire from the high-voltage terminal. The particulate matter detection device of Example 2 held second place with regard to the results for separation of the electric wire from the high-voltage terminal, and the particulate matter detection device of Example 3 held third place with regard to the results for separation of the electric wire from the high-voltage terminal. The particulate matter detection device of Comparative Example 1 showed poor results for separation of the electric wire from the high-voltage terminal. Table 1 clearly shows the difference between the initial capacitance (impedance) and the capacitance after collecting a particulate matter. This suggests that an increase in the amount of particulate matter in exhaust gas can be detected by impedance measurement for one minute.

The particulate matter detection device according to the present invention may be suitably used to immediately detect defects (i.e., abnormality) of a DPF. This makes it possible to contribute to preventing air pollution.

What is claimed is:

1. A particulate matter detection device, comprising:
   a detection device body that extends in one direction and has at least one through-hole that is formed at one end,
   at least one pair of electrodes that are buried in the wall of the detection device body that defines the through-hole, and are covered with a dielectric,
   lines that respectively extend from the pair of electrodes toward the other end of the detection device body, a takeout lead terminal of one electrode of the pair of electrodes, the takeout lead terminal of the one electrode being disposed on the surface of the other end of the detection device body, and connected to the line that extends from the one electrode,
   a takeout lead terminal of the other electrode of the pair of electrodes, the takeout lead terminal of the other electrode being disposed on the surface of the detection device body between the one end and the other end, and connected to the line that extends from the other electrode; and
   an electric wire that is provided with an electric wire securing member at its end, and bonded to the takeout lead terminal of the other electrode through the electric wire securing member,
   wherein the particulate matter detection device being configured so that particulate matter contained in a fluid that flows into the through-hole can be electrically adsorbed on the wall surface of the through-hole by applying a voltage of 50 to 200 kV/cm between the pair of electrodes through the takeout lead terminals using the other electrode as a high-voltage electrode, and the particulate matter adsorbed on the wall surface of the through-hole can be detected by measuring a change in electrical properties of the wall of the detection device body that defines the through-hole.

2. The particulate matter detection device according to claim 1, wherein the electric wire securing member is a metal plate that is bent to sandwich and secure an tip portion of the electric wire.

3. The particulate matter detection device according to claim 2, wherein the electric wire securing member is formed by bending a T-shaped metal plate that includes a rectangular wing area and a rectangular body area that extends from the center of the wing area in the direction perpendicular to the longitudinal direction of the wing area so that each end of the wing area is folded toward the center of the wing area, and the tip portion of the electric wire is sandwiched and secured between each end of the wing area and the center of the wing area.

4. The particulate matter detection device according to claim 2, wherein the electric wire securing member is bonded to the takeout lead terminal of the other electrode through a bonding metal plate.

5. The particulate matter detection device according to claim 2, wherein the electric wire securing member is bonded to the takeout lead terminal of the other electrode through a conductive adhesive.

6. The particulate matter detection device according to 1, wherein the electric wire securing member is a metal paste that covers the tip portion of the electric wire, and the tip portion of the electric wire is bonded to the takeout lead terminal of the other electrode through the metal paste.

7. The particulate matter detection device according to claim 3, wherein the electric wire securing member is bonded to the takeout lead terminal of the other electrode through a bonding metal plate.

8. The particulate matter detection device according to claim 3, wherein the electric wire securing member is bonded to the takeout lead terminal of the other electrode through a conductive adhesive.

* * * * *